(12) United States Patent
Horiuchi (10) Patent No.: US 6,317,511 B1
(45) Date of Patent: Nov. 13, 2001

(54) METHOD AND APPARATUS FOR PARTICLE IMAGE ANALYSIS USING FLOW CELL

(75) Inventor: Hideyuki Horiuchi, Abiko (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 08/803,230

(22) Filed: Feb. 20, 1997

(30) Foreign Application Priority Data

Feb. 22, 1996 (JP) .................................................. 8-034748

(51) Int. Cl.[7] .............................................................. G06K 9/00
(52) U.S. Cl. .............................................. 382/133; 356/39
(58) Field of Search ......................................... 382/133, 134, 382/286; 702/21, 128; 356/23, 39, 335; 250/461.2

(56) References Cited

U.S. PATENT DOCUMENTS

| | | | | |
|---|---|---|---|---|
| 4,786,165 | * | 11/1988 | Yamamoto et al. | 356/23 |
| 5,159,398 | * | 10/1992 | Maekawa et al. | 356/73 |
| 5,159,642 | * | 10/1992 | Kosaka | 382/6 |
| 5,878,160 | * | 3/1999 | Horiuchi et al. | 382/133 |

FOREIGN PATENT DOCUMENTS

| | | | |
|---|---|---|---|
| 4437758-A1 | 4/1995 | (DE) | G01N/15/14 |
| 644 414-A2 | 3/1995 | (EP) | G01N/15/00 |
| 466 168-A2 | 1/1992 | (EP) | G01N/15/14 |
| 551 010-A1 | 7/1993 | (EP) | G01N/15/14 |
| 556 971-A2 | 8/1993 | (EP) | G01N/15/14 |
| 644 416-A1 | 3/1995 | (EP) | G01N/15/14 |
| 660 103-A2 | 6/1995 | (EP) | G01N/15/14 |
| 679 889-A2 | 11/1995 | (EP) | G01N/33/483 |
| 7-83817 | 3/1995 | (JP) | G01N/15/14 |

\* cited by examiner

*Primary Examiner*—Andrew W. Johns
(74) *Attorney, Agent, or Firm*—Mattingly, Stanger & Malur, P.C.

(57) ABSTRACT

A sample is flowed through a flow cell, the passage of particles is detected by a laser light beam, a flash lamp is turned on in response to the detection, still images of the particles are picked up by a TV camera, and the images are image-processed. A particle detection unit adjusting unit calculates the anticipated number of image-processed particles from the total number of detected particles, compares it with the number of actually image-processed particles, and changes a particle detection condition such that the calculated value is equal to the actual measurement value. In actual sample measurement, an operation condition of the apparatus can be determined and measurement result can be corrected using those parameters.

16 Claims, 5 Drawing Sheets

METHOD AND APPARATUS FOR PARTICLE IMAGE ANALYSIS USING FLOW CELL

BACKGROUND OF THE INVENTION

The present invention relates to method and apparatus for particle image analysis, and more particularly to method and apparatus suitable for picking up and analyzing still images of particles suspended in a fluid sample flowed through a flow cell.

In prior art particle image analysis, in order to classify and analyze corpuscles in blood or cells and particles in urine, a sample is prepared on a slide glass and it is observed through a microscope. For the urine, since a particle density in the urine is low, the sample is previously centrifugally concentrated by a centrifugal separator before it is observed.

As a method or apparatus for automating the observation and the inspection procedures, a sample of blood, for example, is applied onto a slide glass which is then mounted on a microscope, and a microscope stage is automatically scanned and stopped at a position where particles are present to pick up a still particle image, and the particles in the sample are classified and analyzed by using feature extraction and pattern recognition methods by image processing techniques.

However, in the above method, it takes a long time to prepare the sample and perform the procedures to find the particles while mechanically moving the microscope stage for moving the particles to an appropriate image read area. Accordingly, a long time is required for the analysis and the mechanical structure is complicated.

As a particle image analysis method or a particle image analysis apparatus which does not need the preparation of the applied sample, a flow cytometer method has been known in which sample particles suspended in fluid are flowed through a flow cell and they are optically analyzed. The flow cytometer method observes a strength of fluorescence or scattered light from each particle in the sample and has a processing ability of 1000 particles per second.

Additionally, an attempt to pick up still particle images of particles in a continuously flowing sample and classifying and analyzing the particles from the respective still particle images has been made. An example thereof is disclosed in JP-A-7-83817.

According to the technique disclosed in JP-A-7-83817, particles picked up in one image which is picked up by an image pick-up unit and particles detected by a particle detection unit are correlated one to one. Thus, particles corresponding to the detected particles of the particles present in the image when a flash lamp light source is lit are counted from the particle detection signal, and the count is correlated to the detected particles of the particles present in the image to discriminate the particles which are not regarded as the detected particles from the detected particles. As a result, a complicated circuit configuration is required.

SUMMARY OF THE INVENTION

It is an object of the present invention to provide a flow type particle image analysis method and a flow type particle image analysis apparatus which facilitate the correlation between particles obtained by a particle detection unit and particle images obtained by a particle image pick-up unit.

According to one aspect of the present invention, there is provided a particle image analysis method for picking up still images of particles as the particles flowing in a flow cell are detected and analyzing the picked-up still images of the particles, comprising a step of flowing fluid having particles suspended therein to the flow cell, a step of counting the number of still images of particles having lager sizes than a predetermined size, of the still images of particles obtained for the fluid, a step of counting the number of particles having larger detection signals than a predetermined level, of the particles detected for the fluid, a step of calculating the anticipated number of particles to be image-processed based on the counted number of particles; and a step of comparing the counted number of still images and the calculated number of particles.

According to another aspect the present invention, there is provided a particle image analysis apparatus having particle detection means for detecting particles in a sample flowing in a flow cell, a light source for emitting a pulsive light in response to the detection of the particle, means for picking up still images of the particles in response to light emission and means for analyzing the picked-up still images of particles; comprising detection condition adjusting unit for receiving a particle detection signal from said particle detection means, characterized in that said detection condition adjusting unit including a) size setting means for setting a lower limit of a size of particle to be image-processed, b) count means for counting the number of still images of particles having larger sizes than the setting set by said size setting means, c) detection signal setting means for setting a magnitude of a signal to be limited, of the output signal from said particle detection means, d) signal count means for counting the number of signals larger than the setting set by said detection signal setting means, e) calculation means for calculating the anticipated number of particles to be image-processed based on information from said signal count means, and f) compare means for comparing the counted number of still images with the calculated number of particles.

DESCRIPTION OF THE PREFERRED EMBODIMENTS

The affect of the frequency characteristic of a particle detection unit in a particle image analysis apparatus having a flow cell varies from apparatus to apparatus. In a semiconductor laser which is commonly used as a laser light source of the particle detection unit, the spread of the laser beam includes a large variation and the beam spot size after being focused by a lens varies from element to element. Namely, a detection condition of the particle detection unit varies from apparatus to apparatus. These are problems encountered in assembling the apparatus. In monitoring the status of the apparatus while the apparatus is being operated, the condition of the apparatus adjusted at the time of assembling of the apparatus may be lost or the malfunction of the laser output or the flash lamp which is commonly used in the particle image pick-up unit may occur. Further, when a sample fluid flow width is wider than an image pick-up area, portions of particles may be cut off around a periphery of the image pick-up area. In order to solve those problems, in accordance with the apparatus shown in FIG. 1, the anticipated number of image-processed particles is determined based on the counted number of particles with consideration of a measurement condition. Since a calculation formula to acquire the anticipated number of image-processed particles may be changed by the measurement condition, the anticipated number of image-processed particles may be determined in order to cope with the change of the measurement condition. The measurement condition may include a sample amount, a flow rate of sample fluid flow, a measurement time and a particle image pick-up condition, and once the condition is determined, the number of image particles may be statistically anticipated.

Preferably, a particle disposal condition is set by an operator based on a particle size in a flow direction of the particle image of interest. In actual adjustment, the particle detection condition is adjusted by changing a particle detection level of the particle detection unit and a pulse width of a particle detection signal. In this manner, the adjustment which considers the variation of the laser output and the variation of the adjustment condition of the optical system which influence to the signal condition of the particle detection unit is attained.

For the number of times pulses of turn-on of the flash lamp, the particle detection unit is adjusted based on the calculated value and the actual number of times of turn-on. Thus, the failure of turn-on of the lamp and the malfunction of the control circuit for the lamp turn-on circuit can be checked.

In a preferred embodiment, the anticipated number of image-processed particles is a mean value of multiple measurements of the same fluid sample. Thus, an adjustment condition with a small statistical variation factor may be set. Further, the anticipated number of image-processed particles may be a mean value of measurements of different fluid samples. In this case, the adjustment condition of the particle detection unit may be grasped without considering a difference between particle densities. This is attained because the evaluation may be made by a ratio of the calculated value and the actual number of image processed particles.

Parameters used in the adjustment are measured before the start of the measurement of the fluid sample. The apparatus condition is grasped based on the measurement result and correction data for the particle analysis is obtained. Thus, the correction of data due to the mismatching between the sample fluid flow and the image pick-up view field can be made.

The parameters used in the adjustment may be measured during the measurement of the actual fluid sample. Whether the operation condition of the apparatus is normal or not is monitored based on the measurement result. In this manner, the adjustment condition and the operation condition of the particle detection unit in the course of particle analysis can be grasped.

Where there are a plurality of measurement modes for the fluid sample, the adjustment is made for each measurement mode. In this manner, the analysis precision of the overall particle image processing may be enhanced.

The present invention is explained specifically although it should be understood that specific examples and restrictive expressions recited in the description are not used to limit the present invention but they are used to simply aid the understanding of the present invention.

Particles in the flow cell which passed through the particle detection area are detected, and after a predetermined time period when the detected particles reach a predetermined position in the still image pick-up area, the flash lamp is lit to pick up the still image of the particles.

It frequently occurs that one picked-up still particle image includes small particles other than the particles detected by the particle detection unit. This phenomenon is prominent as the particle detection signal level is higher. Thus, a method for discriminating the particles to be detected from the picked-up particle image is necessary.

As a principle of detection of the particle detection unit, particles having a signal pulse width larger than a predetermined level, of the particles which exceed the signal level of the particle detection signal, are regarded as the particle detection signals. This pulse width corresponds to a time during which the measured particles pass through the particle detection unit and is proportional to a size of the passed particle.

In order to correlate the particles detected by the particle detection unit to the particles in the still image, the number of anticipated particle images is calculated based on the total number of passed particles detected by the particle detection unit and as many particles as the anticipated number of particles are used in the descending size order from the image-processed particle image. This method is simple in processing and includes less time restriction but the particle feature parameters must be stored until the measurement is completed. For the measurement object which needs to store the particle image, a large image memory is required. In order to solve the problems, particles in the image which have smaller particle sizes than a predetermined size are disposed in a stage of processing one frame of image.

The present invention conforms to the setting of the particle disposal size and the adjustment of the particle detection unit.

Namely, when the particle disposal size is set rather small, the number of particle images to be classified increases, the number of particle feature parameters increases and a larger image memory is required. In this case, since particles other than the detected particles are introduced, the particle classification precision may be affected.

Conversely, when the particle disposal size is set rather large, the number of particle images to be classified decreases and the correlation to the particles detected by the particle detection unit is not correctly done.

Accordingly, the particle detection condition and the particle disposal size for disposing the particles in the image must be adjusted to a proper condition. Further, the particle detection condition must be set and adjusted by considering the affect of the spot size of the laser to be used, the affect of the frequency characteristic of the particle detection circuit and the affect of the scattering characteristic of the scattered particles. The affects are more prominent as the particle size is smaller or the flow rate of the flow system is faster.

When the particle detection level is fixed, the measured pulse width changes with the magnitude of the particle detection signal because the signal amplitude is not normalized, and the variations of the laser output of the particle detection unit, the sensitivity of the detection unit and the optical system adjustment occurs for each apparatus. When the variation factors of the pulse width are considered, it cannot be said that the particle detection operation is constant. Under such a condition, the blocked-out value of the particle size feature amount obtained from the particle image picked up for each apparatus and the pulse width detection value determined by the particle detection unit do not correlate one to one. The adjustment of the particle detection unit for each apparatus is not sufficient. Further, whenever the laser is exchanged or the optical system is readjusted, it is necessary to adjust the particle detection condition of the particle detection unit. A method for correlating the detected particles and the image-processed particles without need for substantially considering the complicated adjustment operation is needed.

The present invention adopts the following method to solve the problems in the particle detection unit and in adjusting the particle disposal size in the image processing.

The same particle detection unit as that described above is presumed. Namely, the light scatter from the particles passed through the particle detection unit is detected by the optical detector, and only those particles having pulse widths not smaller than a predetermined width and particle sizes not smaller than a designated size are selected as the particles detected by the particle detection unit. The total number of detected particles passed during the measurement time are counted and it is set as the total number of detected particles.

The flash lamp light source is lit in response to the detection of the particles to pick up a still image of the detected particles and all particles in the image are image-processed, the particle features necessary for the particle classification are extracted, and the particle classification is conducted. The feature extraction and the particle classification processes are conducted for all image particles picked up during the measurement time. The step to dispose, without image processing, the particles of small sizes which are not necessary for the particle classification is added. The particle size disposed of by this step is hereinafter referred to as a particle disposal size.

At the end of the measurement, the anticipated number of detected image particles in the particle still image by the turn-on of the flash lamp during the measurement time is calculated from the total number of detected particles passed through during the measurement time in the particle detection unit. The number of detected image particles is calculated based on the particle density in the sample, the measurement time and the image pick-up condition of the TV camera. When the anticipated number of detected image particles is given by Ng, a calculation formula for Ng changes with the measurement condition but it may be determined by assuming that events of occurrence of passage of the particles follows the Poason's process in statistics, and it is generally expressed by:

$$Ng=Nf \cdot \gamma \cdot \{\lambda+\exp(-\lambda \cdot (1-h))\} \quad (1)$$

where Nf represents the total number of frame images which can be picked up by the TV camera during the measurement time. When the measurement time is Tm and one frame time is Tf, Nf=Tm/Tf. The term $\gamma$ represents a ratio of the number of frames picked up by the particle detection under the actual sampling condition to Nf, and the content of $\gamma$ varies with the measurement condition. The value Nf·$\gamma$ corresponds to the number of anticipated frames which actually picked up the particle images.

In the formula (1), the content of { ... } represents the anticipated mean number of particles including the detected particles present in the image read area, where $\gamma$ represents the mean number of particles present in a volume Vg corresponding to the volume of the image read area, h represents a value between 0 and 1 which is determined by a particular point in the image read area to turn on the flash lamp by the particle detection, and it is normally set to a value close to 1, and $\gamma$ is expressed by a formula (2). Vm represents the measurement sample volume.

$$\lambda=(Nm/Vm) \cdot Vg \quad (2)$$

A specific formula for $\gamma$ is described below.

Consider a case where the restriction to the turn-on timing of the flash lamp, that is, the restriction to turn on only in the odd or even fields of the TV camera is not imposed and the particle image can be picked up most efficiently. When the image stored in the CCD TV camera is read into the image memory in two fields after the turn-on of the flash lamp, the formula for $\gamma$ is given by:

$$\gamma=2 \cdot \{1-\exp(-Nm \cdot Tf/2 \cdot Tm)\}/\{2-\exp(-Nm \cdot Tf/2 \cdot Tm)\} \quad (3)$$

where Tf represents one frame time of the TV camera. When three fields are required for the image reading and the image processing, in which a dead time increases by one field, the formula for $\gamma$ is given by:

$$\gamma=2 \cdot \{1-\exp(-Nm \cdot Tf/2 \cdot Tm)\}/\{3-2 \cdot \exp(-Nm \cdot Tf/2 \cdot Tm)\} \quad (4)$$

In any case, the formula for $\gamma$ varies with the particle density, the measurement time and the condition of the TV camera image pick-up unit. The anticipated number of detected particles provides a relatively correct number of detected image particles although statistical variation is unavoidable.

In the formula (1), the value Nf·$\gamma$ corresponds to the mean number of times of turn-on of the flash lamp during the measurement time, that is, the mean number of frames of the TV image picked up by the particle detection. Accordingly, by substituting it by the total number of images actually image-processed, that is, the total number of frames $n_f'$ having the particle images picked up, the process becomes simpler. In the formula (1), when Nf·$\gamma$ is substituted by $n_f'$, Ng is given by:

$$Ng=n_f' \cdot \{\lambda+\exp(-\lambda \cdot (1-h))\} \quad (5)$$

As described above, the value Nf·$\gamma$ corresponds to the anticipated number of frames which actually pick up the particle images. It is expressed as:

$$n_f=N \cdot \gamma \quad (6)$$

Depending on the measurement condition, approximation formulas of the formulas (1) to (5) may be introduced to simplify the calculation process.

A specific adjustment method is described below.

First, the particles to be classified are determined, a lower limit of the particle sizes occupied by the particles is determined, and it is set as an upper limit of the particle size to be disposed in the image processing. The particle images having sizes smaller than the disposal size are not considered as the image particles to be processed. Accordingly, the particle image feature parameters and the particle images for those images are not stored.

An appropriate particle detection condition, that is, the particle detection level and the pulse width are determined and the measurement of the particles is started. The total number of particle signals which satisfy the above detection condition is counted in the particle detection unit. At the end of the measurement, the total number of particles passed during the measurement time is obtained. Based on the total number of particles and the measurement condition, the anticipated number of images Ng which would have been processed during the measurement time as the particle images is calculated by using the formulas (1) and (3) or the formula (4).

Then, the anticipated number of images Ng is compared with the total number of particles Ng' which are actually image-processed. If Ng' is larger than Ng, the particle detection condition is set severer to change the particle detection condition not to detect particles having small signals. On the contrary, if Ng' is smaller than Ng, the particle detection condition is set less sever to change the condition to detect more particles by the particle detection unit.

The adjusted condition is to set the detection level of the particle detection unit and the detected pulse width such that Ng is equal to Ng', that is, to set such that Ng'/Ng is equal to 1. However, since the statistical variation is unavoidable in an actual case, it is preferable to set Ng'/Ng to be somewhat larger than 1. It is safer not to determine by one measurement result but determine based on a mean value of a plurality of times of measurements. So long as the determination is made based on Ng'/Ng, the sample of the multiple measurements need not be the same sample.

Alternatively, the particle detection condition of the particle detection unit may be set first and the adjustment work may be conducted for the particle disposal size in the image processing. It is appropriate from the detection condition of the particle detection unit to consider the particle disposal size based on the length along the flow direction of the particles.

When a plurality of particle analysis modes are present, the above adjustment work is needed for each measurement mode. Since the difference in the measurement modes is usually the difference in the particles to be measured, the particle detection conditions are usually different.

The above discussion is applicable when the width of the sample flow is narrower than the width of the still image pick-up unit. However, when the sample flow condition is larger than the image pick-up view field, the particles of certain proportion flow out of the view field and the number of particle images is reduced. Thus, it is necessary to adjust the particle detection condition of the particle detection unit and the disposal size condition of the particle images by taking the reduction into consideration.

In the flow type particle image analysis apparatus, the operation condition of the flow type image analysis apparatus may be checked by using various parameters used in the adjustment means.

Since the number of image-processed particles anticipated from the total number of passed particles can be calculated from the count of the total number of particles passed through the particle detection unit during the measurement time, this value is compared with the total number of image-processed particle images. If the anticipated number of image particles by the calculation is larger than the number of particles actually image-processed, it is okay. However, if the number of particles actually image-processed is smaller, it is determined whether it is due to the statistical error or a problem in the apparatus. If no problem is found, the number of particles is corrected based on the normal classification result and the classification ration. If a problem is involved, the correction of the number of particles is stopped and the presence of problem is noticed to the operator.

This condition may be caused by the reduction of the output of the particle detection laser, a trouble in the particle detection unit, misadjustment and the failure of turn-on of the flash lamp. When the laser is replaced or the apparatus is readjusted, the above parameters may be checked as means to check whether the apparatus operates normally and as readjustment means to grasp the adjustment condition.

For the failure of the turn-on of the flash lamp, the ratio of the number of times of actual turn-on of the flash lamp to the number of times of the pulsive turn-on anticipated by the formula (6) to determine the condition of the control unit for the lamp and the lifetime of the lamp. Namely, it may be conducted for the total number of frames which pick up the particle images during the measurement time. The anticipated number of image-processed frames may be calculated from the formula (6) based on the count of the total number of frames which pick up the particle images during the measurement time, and this value is compared with the number of image frames actually processed to determine the condition of the apparatus. A deviation from the calculated value may occur due to mistiming of the control unit for the turn-on of the flash lamp.

In this manner, by comparing the anticipated number of image-processed particle images and the anticipated number of image frames with the number of actual particle images and the number of image frames, whether the apparatus operate normally or a trouble occurs can be determined.

By conducting the above check operation of the apparatus before the start of measurement of the flow type particle image analysis apparatus and measuring the parameters to grasp the condition of the apparatus and obtain various correction data, the reliability of the measurement apparatus is improved and the correction condition of the measurement data can be obtained.

The above check operation of the apparatus may be conducted by measuring the parameters for each measurement sample during the measurement of the actual samples by the flow type particle image analysis apparatus to monitor whether the operation condition of the apparatus is normal or not. If the statistical variation is large, a mean value for a plurality of samples may be calculated to examine the adjustment condition of the apparatus. In this case, the measurement samples need not be of the same type or of the same particle density.

When a plurality of modes are present in the sample measurement mode, it is necessary to measure and adjust the above parameters for each measurement mode.

Referring to FIGS. 1 to 5, an embodiment is explained.

Figure 1:
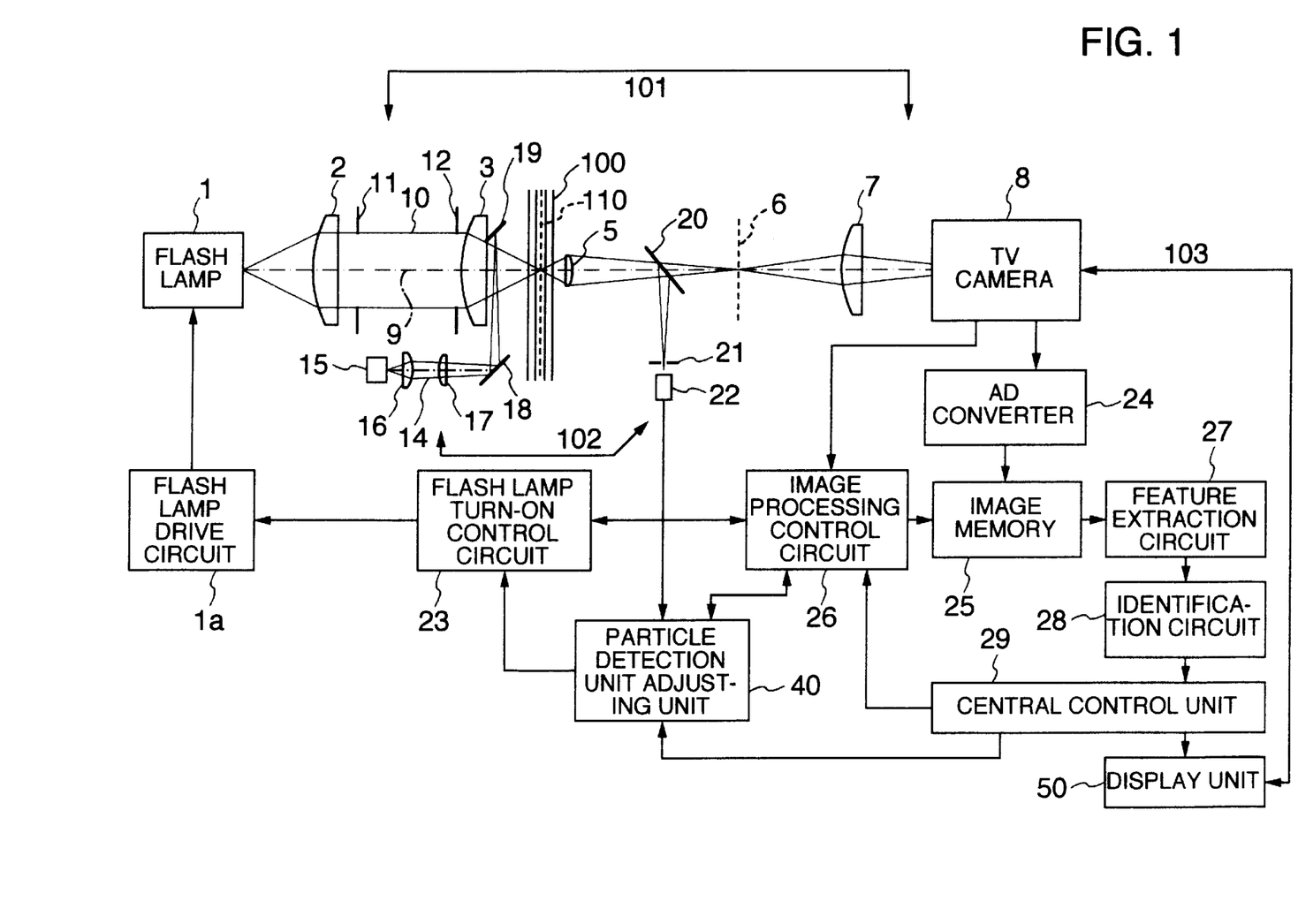
FIG. 1 shows a general configuration of a flow type particle image analysis apparatus in accordance with one embodiment of the present invention.

In FIG. 1, numeral 100 denotes a flow cell, numeral 101 denotes an image pick-up unit, numeral 102 denotes a particle detection unit, numeral 103 denotes a particle analysis unit, numeral 1 denotes a flash lamp, numeral 1a denotes a flash lamp drive circuit, numeral 2 denotes a field lens, numeral 3 denotes a microscope condenser lens, numeral 5 denotes a microscope object lens, numeral 6 denotes a focusing position, numeral 7 denotes a projection lens, numeral 8 denotes a TV camera, numeral 11 denotes a view field iris, numeral 12 denotes an aperture iris, numeral 15 denotes a semiconductor laser, numeral 16 denotes a collimator lens, numeral 17 denotes a cylindrical lens, numeral 18 denotes a reflection mirror, numeral 19 denotes a microreflection mirror, numeral 20 denotes a beam splitter, numeral 21 denotes an iris, numeral 22 denotes an optical detection circuit, numeral 23 denotes a flash lamp turn-on control circuit, numeral 24 denotes an AD converter, numeral 25 denotes an image memory, numeral 26 denotes an image processing control circuit, numeral 27 denotes a feature extraction circuit, numeral 28 denotes an identification circuit, numeral 29 denotes a central control unit, numeral 40 denotes a particle detection unit adjusting unit, and numeral 50 denotes a display unit.

The flow type particle image analysis apparatus in accordance with the embodiment of FIG. 1 comprises the flow cell 100 to which sample fluid having particles suspended therein is supplied, the image pick-up means 101 for picking up the image of the sample fluid in the flow cell 100, the particle detection means 102 for detecting the particles form the picked-up image and the particle analysis means 103 for analyzing the detected particles.

The flow cell 100 is supplied with sheath fluid together with the sample fluid so that the sample fluid forms a flow encompassed by the sheath fluid. The sample fluid flow 110 becomes a stable steady flow, a so-called sheath flow having a flat sectional shape perpendicularly to a microscope optical axis 9 (to be described later) of the image pick-up means 101 (to be described later), and it flows from the top to the bottom of the drawing at the center of the flow cell 100. A flow rate of the sample fluid flow 110 is controlled by the central control unit 29 (to be described later).

The image pick-up unit 101 functions as the microscope and comprises the flash lamp 1 which serves as the pulse light source, the flash lamp drive circuit la for lighting the flash lamp 1, the field lens for collimating the pulse light beam from the flash lamp 1, the microscope condenser lens 3 for focusing the collimated pulse light beam 10 from the field lens 2 to the sample fluid flow 110 in the flow cell 100, the microscope object lens 5 for condensing the pulse light beam irradiated to the sample fluid flow 110 in the flow cell 100 and focusing it to the focusing position 6, the TV camera 8 for converting the particle images at the focusing position 6 projected through the projection lens 7 to an image data signal which is a read electrical signal by a so-called interlace method, the view field iris 11 and the aperture iris 12 for limiting the width of the pulse light beam 10. As the TV camera, a CCD camera which exhibits a low degree of residual image is commonly used.

The particle detection unit 102 comprises the semiconductor laser 15 which is the detection light source for emitting a laser beam as a detection light, the collimator lens 16 for collimating the laser beam from the semiconductor laser 15 to the collimated laser beam 14, the cylindrical lens 17 for focusing only one direction of the laser light beam 14 from the collimator lens 16, the reflection mirror 18 for reflecting the laser light beam 14 from the cylindrical lens 17, and the micro-reflection mirror 19 disposed between the microscope condenser lens 3 and the flow cell 100 for guiding the laser light beam 14 from the reflection mirror 18 to the neighborhood of the upstream of the image read area on the sample fluid flow 110.

The particle detection unit 102 comprises the microscope object lens 5 for condensing the scattered light of the laser light beam 14 by the particles (the microscope object lens 5 being shared with the focusing microscope object lens 5 of the image pick-up means 101), the beam splitter 20 for reflecting the scattered light condensed by the microscope object lens 5, the optical detection circuit 22 for receiving the scattered light from the beam splitter 20 through the iris 21 and outputting an electrical signal representing the intensity thereof, and the flash lamp turn-on control circuit 23 for activating the flash lamp drive circuit la in accordance with the electrical signal from the optical detection circuit 22.

The particle analysis unit 103 comprises the AD converter 24 for converting the image data signal transferred from the TV camera 8 to a digital signal, the image memory 25 for storing the data based on the signal from the AD converter 24 to a predetermined address, the image processing control circuit 26 for controlling the writing and the reading of the data in the image memory, the feature extraction circuit 27 for conducting the image processing in accordance with the signal from the image memory 25 and extracting the classes and the number of particles, the identification circuit 28, the central control unit 29, the particle detection unit adjusting unit 40 for determining the number of particles in the sample fluid 110 and adjusting the particle detection unit, and the display unit 50 for displaying the number of particles and the classification which are results of the image processing.

The central control unit 29 is constructed to control the image pick-up condition of the TV camera 8 and the condition of the flow of the sample fluid in the floe cell 100, control the image processing circuit 26, store the image process result from the identification circuit 28, exchange the data with the particle detection unit adjusting unit 40 and display the data on the display unit 50.

Figure 2:
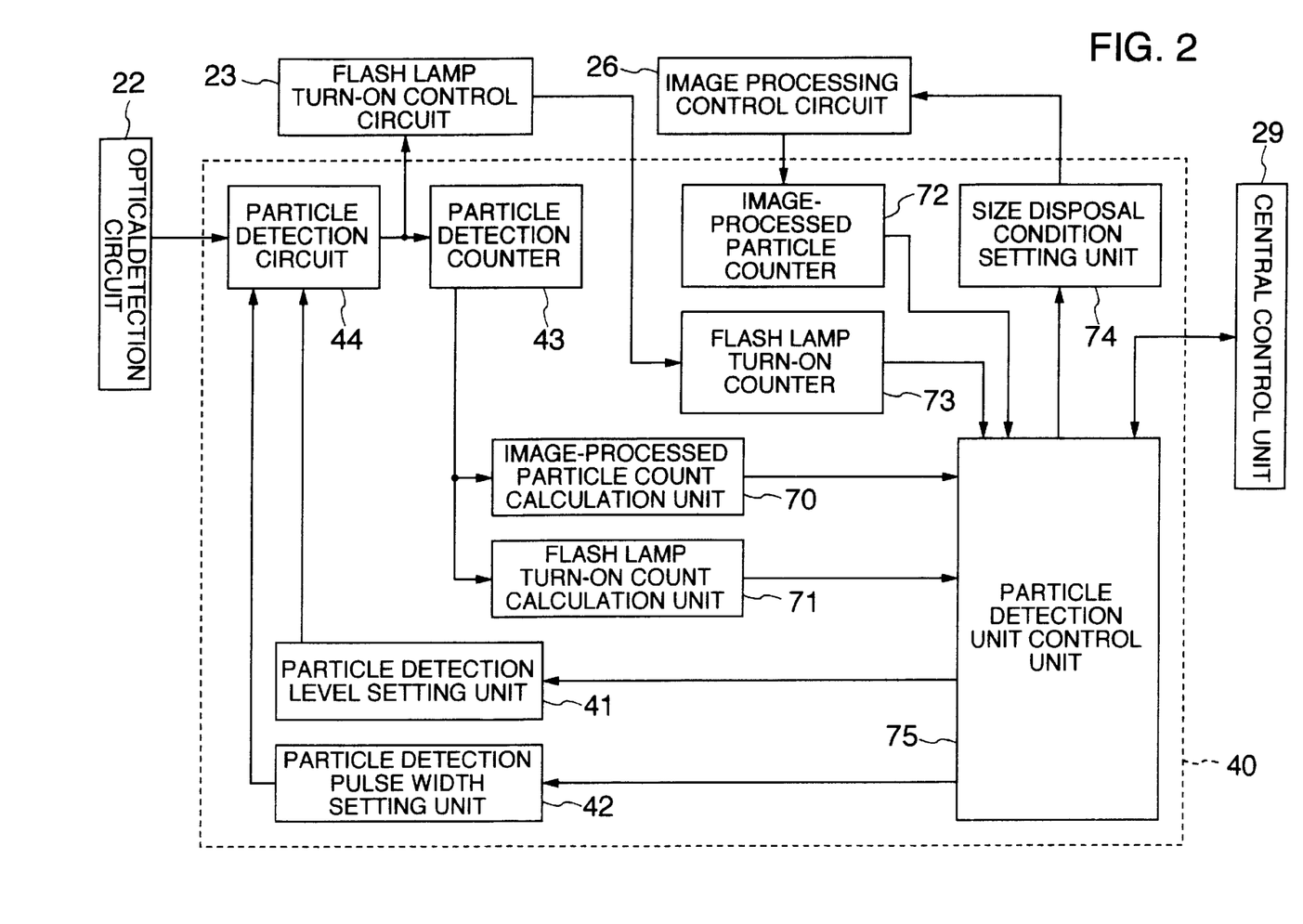
FIG. 2 shows a block diagram of a configuration of a particle detection unit adjustment unit in the apparatus of FIG. 1.

Referring to FIG. 2, the configuration of the particle detection unit adjusting unit 40 is explained. In FIG. 2, the like elements to those shown in FIG. 1 are designated by the like numerals and the explanation thereof is omitted.

In FIG. 2, numeral 44 denotes a particle detection circuit, numeral 41 denotes a detection level setting circuit, numeral 42 denotes a detection pulse width setting unit, numeral 43 denotes a detected particle counter, numeral 70 denotes a particle image count calculation unit, numeral 71 denotes a flash lamp turn-on count calculation unit, numeral 72 denotes a particle image count unit, numeral 73 denotes a flash lamp turn-on count unit, and numeral 74 denotes a size disposal condition setting unit.

In FIG. 2, the particle detection circuit 44 of the particle detection unit adjusting unit 40 detects a particle detection signal which is not smaller than a predetermined signal level, from the optical detection circuit 22. The particle detection level of the particle detection circuit 44 is compared with the detection condition set by the detection level setting unit 41 and the detection pulse width setting unit 42, and those signals which meet the condition are regarded as the particle detection signals. The detected particle counter 43 counts the number of pulses detected by the particle detection circuit 44. At the end of the measurement, the count of the detected particle counter 43 represents the total number of particles passed through the detection unit.

By using the particle count Nm of the detected particle counter 43 at the end of the measurement of each sample, the number of image-processed particles Ng which are anticipated to be image-processed during the measurement time is calculated by the particle image count calculation unit 70 and the number of times of turn-on nf which is anticipated for the turn-on of the flash lamp during the measurement time is calculated by the flash lamp turn-on count calculation unit 71.

On the other hand, the number of particle images Ng' actually image-processed during the measurement time and the actual number of times of turn-on of the flash lamp nf' are set to the particle image count unit 72 and the flash lamp turn-on count unit 73 from the image processing control circuit 26 and the flash lamp turn-on control circuit 23, respectively.

For the small size particles in the particle image, the image processing is suspended based on the condition of the size disposal condition setting unit 74 during the image processing.

The detection unit control unit 75 controls the particle detection condition and the size disposal condition in the image processing, compares the calculation count nf and the Nf at the end of the measurement with the actual measurements nf' and Ng', and controls the overall particle detection unit adjusting unit such as the change of the particle detection condition.

Since the detected particle counter 43 counts the total number of particles detected within the measurement time, this count is used to calculate the total anticipated number of particle images which are actually image-processed within the measurement time, by the particle image count calculation unit 70 by using a predetermined mathematical formula. The calculation formula is influenced by the measurement condition. Examples of the calculation formula is shown by formulas (1) to (4). The flash lamp turn-on count calculation unit 71 has a function to calculate the anticipated total number of frames picked-up by the TV camera during the measurement time. A calculation formula (6) is used.

The flow type particle image analysis method of the above construction and the flow type image analysis apparatus used therefor are explained below.

The operations of the image pick-up means 101 and the particle detection means 102 are first explained. The semiconductor laser 15 continuously oscillates and the passage of the particles in the flow of the sample fluid 110 through the detection area is always observed.

The laser light beam 14 from the semiconductor laser 15 is converted to the collimated laser light beam by the collimator lens 16 and only one direction of the light beam 14 is focused by the cylindrical lens 17. The laser light beam 14 is reflected by the reflection mirror 18 and the micro-reflection mirror 19 and irradiated to the sample fluid flow 110 in the flow cell 100. The irradiation position is the particle detection position at which the laser light beam 14 is focused by the cylindrical lens 17, and it is the position in the neighborhood of the upstream of the image read region on the sample fluid flow 110.

When the particles to be analyzed traverse the laser light beam 14, the laser light beam 14 is scattered. The scattered light of the laser light beam is reflected by the beam splitter 20 and detected by the optical detection circuit 22 which converts it to an electrical signal in accordance with the strength thereof. The output of the optical detection circuit 22 is sent to the particle detection unit adjusting unit 40 which takes those signals not smaller than a predetermined level and a predetermined pulse width as the detected particles and outputs the result to the flash lamp turn-on control circuit 23. When the particle detection is made, it is assumed that the particles to be image-processed have passed and the detected signals are transmitted to the flash lamp turn-on control circuit 23. A predetermined delay time is determined by a distance between the particle detection position and the image read area and the flow rate of the sample fluid 110.

When the flash lamp turn-on signal is transmitted to the flash lamp drive circuit la, the flash lamp drive circuit la turns on the flash lamp 1. The pulse light emitted by the flash lamp 1 travels on the microscope optical axis 9, collimated by the field lens 2, focused by the microscope condenser lens 3 and irradiated to the sample fluid flow 110 in the flow cell 100.

The width of the pulse light beam 10 is limited by the view field iris 11 and the aperture iris 12.

The pulse light beam irradiated by the sample fluid flow 110 in the flow cell 100 is focused by the microscope object lens 5 and focused to the focusing position 6. The image at the focusing position 6 is projected to the image pick-up plane of the TV camera 8 by the projection lens 7 and it is converted to the image data signal by the interlace method. In this manner, the still particle images of the particles in the sample fluid flow 110 are picked up. The image pick-up condition in the TV camera 8 is preset in the central control unit 29 and the image pick-up operation of the TV camera 8 is controlled by the image pick-up condition.

The particle analysis unit 103 is now explained.

The image data signal picked up by the TV camera 8 and converted by the interlace method is converted to the digital signal by the AD converter 24, and the resulting data is stored at a predetermined address of the image memory 25 under the control of the image processing control circuit 26. The data stored in the image memory 25 is read under the control of the image processing control circuit 26 and applied to the feature extraction circuit 27 and the identification circuit 28 for the image processing, and the result thereof is stored in the central control unit 29. The contents stored in the central control unit 29 are the particle identification feature parameters used for the particle classification and the particle classification result data. The classification identification processing of the particles is automatically conducted by the conventional pattern recognition process. The image processing result, the measurement condition and the number of images image-processed are sent from the image processing control circuit 26 to the particle detection unit adjusting unit 40.

Figure 3:
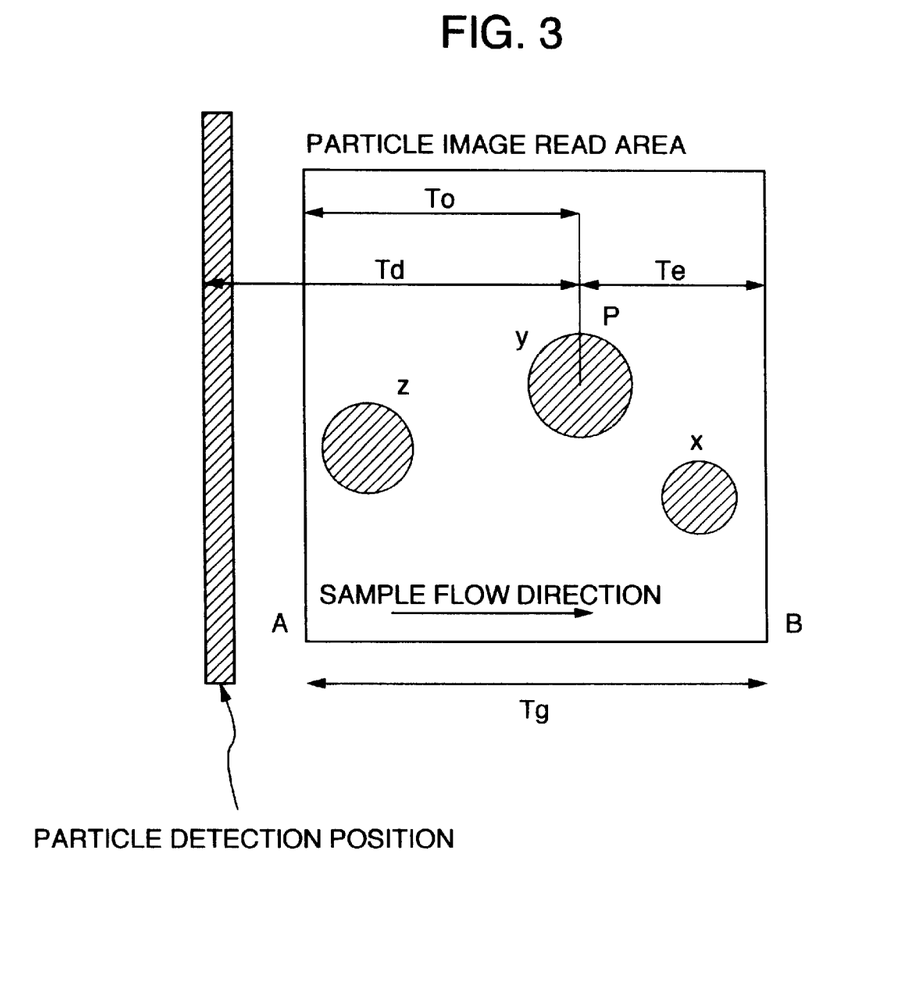
FIG. 3 illustrates the detection of particles and the reading a still image of the particles.

Referring to FIG. 3, a relation between the particle detection position and the still particle image read position in one image particle count is explained. An abscissa in FIG. 3 represents the sample fluid flow direction.

As shown in FIG. 3, assuming that Tg represents a time required for the particle to flow from an end B to an end A of the image, Te represents a time required for the particle to flow from the flash lamp turn-on position P of the still particle image read view field to the end B, and To represents a time required for the particle form the end A of the image to the flash lamp turn-on position P, the following relation is met:

$$Tg=Te+To$$

When the particles in the measurement sample pass the particle detection position and the particle detection signal is not smaller than the predetermined level, the detection pulse signal is outputted. After the elapse of a delay time Td for the particle to reach the predetermined position in the still particle image read area after the detection pulse signal has been outputted, the flash lamp 1 is turned on.

The turn-on condition of the flash lamp 1 is as follows:

After the completion of the reading of the still particle image by the particle detection of the immediately earlier cycle, namely, after the turn-on of the flash lamp 1 after the turn-on of the flash lamp 1 is inhibited and the image signal is transferred by one still particle image by two field read signals, the flash lamp 1 is again rendered to be ready to turn on. This is made by a lamp turn-on ready signal which is generated by the flash lamp control circuit 23. If the signal level of the lamp turn-on ready signal is "on", the flash lamp 1 is ready to turn on, and if the signal level is "off", the flash lamp 1 is inhibited from the turn-on.

Figure 4:
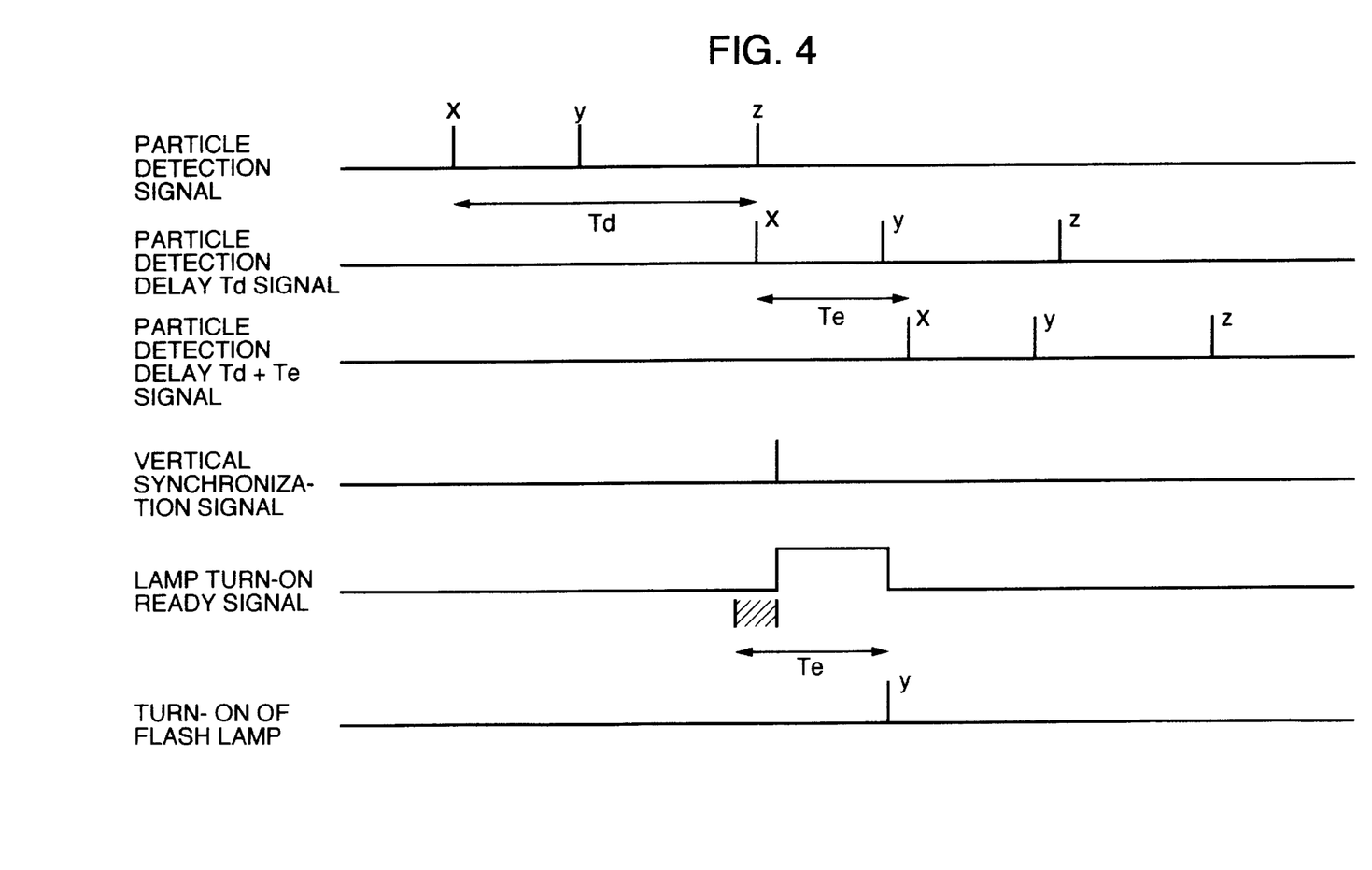
FIG. 4 illustrates a timing relation of signals when one particle image is counted.

In FIG. 4, the flash lamp 1 is turned on after the elapse of the time Td from the detection of the particle y, but it may be possible that particles passed before the detection of the particle y are present downstream of the flow.

As such particle, the particle x which is present at the position of the time interval Te before the passage of the particle y may be considered since the lamp turn-on ready signal is not yet "on" during the time Te in which the sample particles flow from the point P to the end B. This appears prominently when the particle density in the sample is high.

A section in which such condition occurs is shown in FIG. 4 by a hatched section of the lamp turn-on ready signal.

When the time from the "on" of the lamp turn-on ready signal to the turn-on of the lamp is larger than Te, the downstream particle, for example, the particle x flows out of the image screen and the hatched area disappears. The time interval of one image particle count is the time Tg in which the particle passes through the still particle image read area.

The timing of the signals is explained with reference to FIG. 4.

It is assumed that the detection signals are generated from three particles x, y and z. In order to timely turn on the flash lamp 1, the particle detection delay Td signal which is delayed by the time Td after the detection of the particle is sent.

Whether the lamp turn-on ready signal is "on" or "off" or whether the lamp is to be turned on or not is determined.

In FIG. 4, since the still particle image was being read in the immediately previous frame, the lamp turn-on ready signal is not "on" from the beginning and the lamp turn-on ready signal is rendered "on" by the vertical synchronization signal. Thus, the flush lamp is not turned on by the particle x and it is turned on by the next particle y, and the lamp turn-on ready signal becomes "off".

Referring to FIG. 2, the particle detection unit adjusting unit 40 is explained.

The particle detection counter 43 compares the particle detection signal from the optical detection circuit 22 with the particle detection level setting unit 41 and the particle detection pulse width setting unit 42, regards the particle having a size larger than the setting conditions as the detected particle, and obtains the total number of detected particles at the end of the measurement. Based on the total number of detected particles, the number of particle images image-processed which is anticipated from the total number of passed particles and the number of times of turn-on of the flash lamp are calculated by the image-processed particle count calculation unit 70 and the flash lamp turn-on count calculation unit 71 by using the above calculation formulas. The calculated values are compared with the number of particle images actually image-processed and the actual number of times of turn-on of the flash lamp by the particle detection unit control unit 75. Specifically, the magnitudes of the calculated values and the actual values are compared.

Noticing to the number of image-processed particles, if the calculated value is larger than the actual value, it means that the particles have been disposed in the stage of the particle image processing by some reason. Namely, in the image processing stage, it is considered that the disposal size set by the size disposal condition setting unit is larger than the particle detection condition set by the particle detection unit. On the contrary, if the calculated value is smaller than the actual value, this means that the particle disposal condition in the image processing is set to a condition to image-process even small particles.

Accordingly, it is the best way to adjust the particle detection condition of the particle detection unit and the size disposal condition of the particle images set by the image processing unit such that the value of the number of image-processed particles calculated from the total number of detected particles and the number of particle images actually image-processed are equal. By adjusting the particle detection unit and the size disposal condition in the image processing to meet the above condition, the detected particles in the particle detection unit and the image-processed particles can be correlated.

In actual, the setting of the particle detection unit and the size disposal condition in the image processing is conducted in the following manner. First, in the image processing, the particles to be processed are determined. When the particles to be processed are determined, the minimum particle size of the particles is determined. When the flow type particle image processing is considered, it is appropriate to set the size disposal condition based on the diameter in the particle flow direction. When the disposal condition of the particle image is determined, the detection condition of the particle detection unit is then set. The particle detection level is set to a level which allows the detection of only the desired particle without detecting small particles, and the particle detection pulse width is first set to an appropriate value. Under this condition, the counting of the particles and the image processing are conducted once and the anticipated number of image-processed particles is calculated by the image-processed particle count calculation unit 70 based on the count of the particle detection counter 43 by using the above calculation formula. The calculated value is compared with the number of particle images actually image-processed. The magnitude relation of the calculated value and the actual value is calculated. When the two values are equal, it means that the adjustment is in good condition for the detection condition of the particle detection unit and the size disposal condition in the image processing. If they are not equal, the particle detection pulse width setting unit 42 is changed in the direction to cause the matching and the particle sample is measured again. The above process is repeated until the calculated value and the actual value match. The comparison of the magnitudes and the control of the particle detection pulse width are conducted by the particle detection unit control unit 75.

Figure 5:
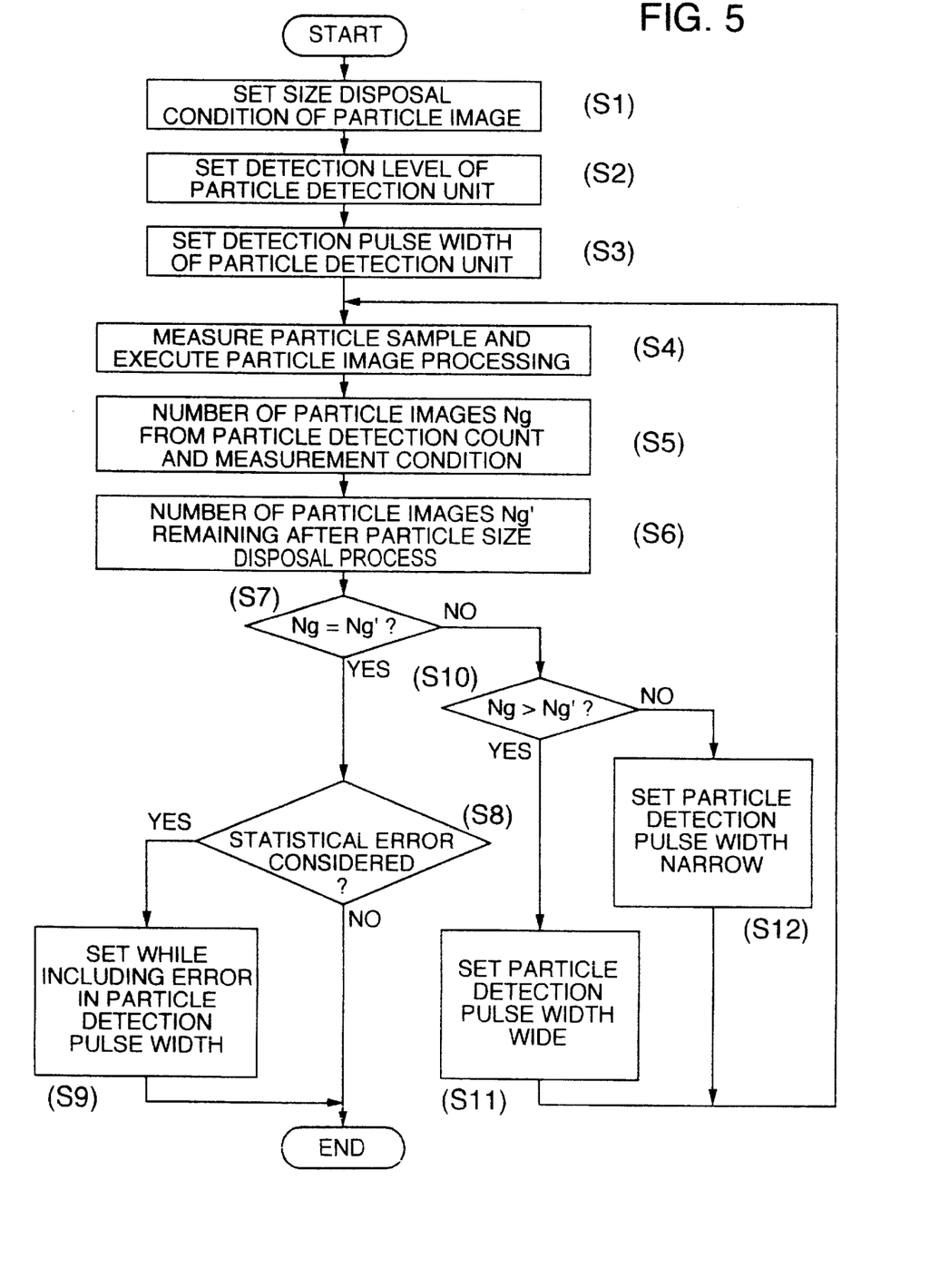
FIG. 5 shows a flow chart for illustrating a particle detection operation in the apparatus of FIG. 1.

The contents described above are explained with reference to the flow chart of FIG. 5. The adjustment steps of the particle detection unit in FIG. 5 are as follows:

First step (S1): Considering the size condition of the particle sample to be image-processed, the particle size disposal condition in the particle image processing is set. The image processing is not conducted for the particles not larger than that size.

Second step (S2): The detection level of the particle detection unit is set. The detection level is determined by considering the magnitude of the signal in the particle detection unit and not to detect a background noise component or a small size noise.

Third step (S3): An initial value of the particle detection pulse width of the particle detection unit to be determined is set. A particle detection signal with not larger than that pulse width is regarded as signal of particle not to be measured, and it is disposed in the particle detection stage.

Fourth step (S4): Fluid sample having particle suspended therein is flown to the flow cell and the particle images are continuously picked up and image-processed.

Fifth step (S5): When the measurement is completed, the number of image particles Ng which would have been image-processed in the particle image processing is calculated by using the total number of particles detected by the particle detection unit, that is, the particle detection value Nm and the measurement condition. The formulas (1) and (5) are used for the calculation formulas.

Sixth step (S6): The number of particle images Ng' remaining without being disposed by the size disposal condition in the actual image processing is examined.

Seventh step (S7): Whether the particle detection condition of the particle detection unit fits to the size disposal condition in the image processing or not is determined. In FIG. 5, whether Ng and Ng' are equal or not is determined. Since it is rare that they are strictly equal, it is practical to set a certain width and determine whether the difference is within that width or not. If Ng and Ng' are equal, it is determined that the adjustment is completed. Before the completion, the following eighth step is executed. If Ng=Ng' is not met, the tenth step is executed.

Eighth step (S8): In order to finally determine the pulse width setting condition of the particle detection, whether a statistical error is to be considered or not is determined.

Ninth step (S9): When the error is considered in the eighth step, the particle detection pulse width is somewhat reduced and the number of particle detection is increased to take the statistical variation into consideration.

Tenth step (S10): The magnitudes of Ng and Ng' are compared. If Ng is larger than Ng', the eleventh step is executed, and if Ng is smaller than Ng', the twelfth step is executed.

Eleventh step (S11): This step is started when the particles of smaller size than the particle detection condition of the particle detection unit are detected and the anticipated number of particles become larger but the number of particles actually remain in the image processing is small. In this case, the setting is adjusted to make the particle detection condition severer, that is, to widen the particle detection pulse width. With the newly set particle detection condition, the process returns to the fourth step to repeat the above steps.

Twelfth step (S12): This step is started when only large particles are detected by the particle detection condition of the particle detection unit and the anticipated number of particle images is calculated smaller but the number of particles actually remain in the image processing is large. In this case, the particle detection condition is adjusted to make the particle detection condition less severe, that is, to narrow the particle detection pulse width and the process returns to the fourth step to repeat the above steps.

In the illustrated flow chart, the detection pulse width of the particle detection unit is changed to adjust the particle detection unit although the same is applicable when the particle detection level is changed or both the detection pulse width and the detection level are changed.

Instead of the adjustment of the anticipated number of image particles, the counted number of still images (the number of particles to be processed) may be adjusted, or if necessary, both may be adjusted.

In actual, since the calculated value is mere anticipated mean value, the actual measurement value includes a statistical variation. Thus, the matching to the calculated value is preferably determined by taking the variation into consideration. Further, the error may be reduced by determining based on the mean value of a plurality of times of measurement. When the statistical variation is taken into consideration, it may be better to set the number of the particle image which is the actual measurement value to be somewhat larger than the calculated value.

By determining based on a ratio of the actual measurement value to the calculated value, the adjustment condition of the particle detection unit can be determined without regard to the particle density. If the ratio is 1, it is in the well adjusted condition.

In the above adjustment method, the size disposal condition in the image processing is fixed and the particle detection pulse width is changed to adjust the particle detection unit. Conversely, the object of the present invention may be attained by fixing the particle detection pulse width and changing the disposal size in the image processing.

By using the same procedures as the adjustment means described above, the anticipated number of image-processed particles is calculated from the total number of passed particles, and when the number of particle images remaining as the particle to be processed is smaller than the number of image particles anticipated from the total number of particles passed during the measurement time, the ration thereof may be calculated to produce a correction constant which is to be reflected to the particle classification and analysis result. Such a phenomenon may occur when the sample flow is deviated from the image pick-up view field of the TV camera and a portion of the particle images is not correctly picked up. It may also occur when the number of times of turn-on of the flash lamp is not proper due to a trouble in the control unit. In such cases, the number of particle images is smaller than the anticipated number of images by the calculation and the correct particle classification and analysis result is not obtained, but by calculating the reduction factor of the number of images, it may be reflected to the particle classification and analysis result.

The operation status of the particle image analysis apparatus may be monitored based on the reduction factor of the number of images. When the factor changes beyond the statistical variation range, it is considered that an abnormal condition exists in the position variation of the sample flow or the control of the flash lamp turn-on control unit.

In the above description, the number of particle image has been noticed. Alternatively, the number of times of turn-on of the flash lamp may be noticed to adjust the particle detection unit.

The total number of particles passed during the measurement time is counted by the detected particle counter 43, and the number of times of turn-on of the flash lamp anticipated from the total number of particles passed through the particle detection unit and the measurement condition is calculated by the flash lamp turn-on count calculation unit 71. The actual number of times of turn-on of the flash lamp is counted by the flash lamp turn-on count calculation unit 73. The anticipated number of times of turn-on of the flash lamp and the actual number of times of turn-on of the flash lamp are compared to adjust the detection condition of the particle detection unit. Further, it may be used to detect the adjustment condition of the particle detection unit and the trouble in the control unit. When the actual number of times of turn-on of the flash lamp is steadily smaller than the calculated value, the ratio thereof may be used to correct the particle analysis data.

For the calculation of the number of times of turn-on of the flash lamp anticipated from the total number of particles passed through the particle detection unit and the measurement condition, the formula (6) is used.

Since the statistical variation is unavoidable as it is for the number of images, the mean value of a plurality of particle samples may be used for evaluation. By calculating a ratio of the calculated value and the actually measured value, the above operation may be conducted by using different particle samples.

In the above flow type particle image analysis apparatus, the operation condition of the flow type image analysis apparatus may be checked by using various parameters used in the adjustment steps. For the parameters, the number of detected particles, the calculated value of the number of image-processed particles, the actual number of image-processed particle images, the calculated value of the number of times of turn-on of the flash lamp, the actual number of times of turn-on of the flash lamp, and secondary parameters calculated from those values, for example, the ratio of the actual measurement value to the calculated value may be used.

Before the start of the measurement of the above flow type particle image analysis apparatus, the various parameters described above may be measured to grasp the condition of the apparatus and for use as the correction data.

During the measurement of the actual sample by the above flow type particle image analysis apparatus, the various parameters described above may be measured to monitor whether the operation condition of the apparatus is normal or not.

When a plurality of sample measurement mode are present, the adjustment may be made for each measurement mode or the operation check for the apparatus may be executed for each measurement mode.

The flow type particle image analysis method and the flow type particle image analysis apparatus in accordance with one embodiment of the present invention are effective for the classification and analysis of the biological samples and cells suspended in fluid, blood cell components such as red blood cells and white blood cells in blood, or urine sedimentation components present in urine.

Particularly, in counting the number of particles of the urine sedimentation components in the urine and classifying the particles, the numbers of particles of the respective samples may differ by several orders or more. Thus, the image processing for the particles detected by the particle detection means is effective in obtaining the information on the number of particles in the sample fluid.

However, in the urine sedimentation components, the types and the sizes of the particles are in wide variety and it is not possible to correctly correlate the detected particles of the particle detection unit and the particles in the still particle image, but according to the present embodiment, the correct particle count, particle classification and particle density may be analyzed.

While the laser light beam from the semiconductor laser is used for the particle detection by the particle detection unit and the laser light beam scattered by the particles are utilized in the present embodiment, the present invention is not limited thereto but it may be applied to a method for detecting the particles by a one-dimension image sensor in which the fluorescence or transmitted light from the particles may be used, or a method for detecting the particles by a change of an electrical resistance by the passage of the particles.

While the interlace method has been described above as the TV camera image pick-up method in reading the image, the operation and the effect of the present invention remain same when a non-interlace scan method is used.

What is claimed is:

1. A particle image analysis method for picking up still images of particles as the particles flowing in a flow cell are detected and analyzing the picked-up still images of the particles, comprising the steps of:
   a) flowing fluid having particles suspended therein to the flow cell;
   b) counting the number of still images of particles having larger sizes than a predetermined size, of the still images of particles obtained for the fluid;
   c) counting the number of particles having larger detection signals than a predetermined level, of the particles detected for the fluid;
   d) calculating the anticipated number of particles to be image-processed based on the counted number of particles; and
   e) comparing the counted number of still images and the calculated number of particles.

2. A particle image analysis method according to claim 1 wherein the predetermined level of the detection signal is a width of the detection signal and/or a level of the detection signal.

3. A particle image analysis method according to claim 2 further comprising the step of:
   changing at least one of the particle size, the width of the detection signal and the level of the detection signal as limiting conditions such that the counted number of still images and the calculated number of particles substantially match.

4. A particle image analysis method according to claim 3 further comprising the step of:
   flowing the fluid sample to be measured to the flow cell after the substantial match of the counted number of still images and the calculated number of particles.

5. A particle image analysis method according to claim 1 further comprising the step of:
   turning on a flash lamp in response to the detection of particles flowing in the flow cell and counting the number of times of turn-on of the flash lamp during the measurement time of the fluid.

6. A particle image analysis method according to claim 5 further comprising the steps of:
   calculating the anticipated number of times of turn-on of the flash lamp based on the counted number of particles; and
   comparing the calculated anticipated number of times of turn-on with the counted number of times of turn-on.

7. A particle image analysis apparatus for executing the method according to claim 1.

8. A particle image analysis apparatus having particle detection means for detecting particles in a sample flowing in a flow cell, a light source for emitting a pulsive light in response to the detection of the particle, means for picking up still images of the particles in response to light emission and means for analyzing the picked-up still images of particles; comprising:
   detection condition adjusting unit for receiving a particle detection signal from said particle detection means,
   characterized in that said detection condition adjusting unit including:
   a) size setting means for setting a lower limit of a size of particle to be image-processed;
   b) count means for counting the number of still images of particles having larger sizes than the setting set by said size setting means;
   c) detection signal setting means for setting a magnitude of a signal to be limited, of the output signal from said particle detection means;
   d) signal count means for counting the number of signals larger than the setting set by said detection signal setting means;
   e) calculation means for calculating the anticipated number of particles to be image-processed based on information from said signal count means; and
   f) compare means for comparing the counted number of still images with the calculated number of particles.

9. A particle image analysis apparatus according to claim 8 wherein said size setting means or said detection signal setting means changes the setting such that the counted number of still images and the calculated number of particles substantially match.

10. A particle image analysis apparatus according to claim 8 wherein said detection signal setting means includes means for setting a level of the output signal and means for setting a width of the output signal.

11. A particle image analysis apparatus according to claim 8 further comprising:
   count means for counting the number of times of turn-on of said light source during the measurement time of the fluid having particles suspended therein.

12. A particle image analysis apparatus for executing the method according to claim 2.

13. A particle image analysis apparatus for executing the method according to claim 3.

14. A particle image analysis apparatus for executing the method according to claim 4.

15. A particle image analysis apparatus for executing the method according to claim 5.

16. A particle image analysis apparatus for executing the method according to claim 6.

* * * * *